United States Patent [19]
Turtakovsky et al.

[11] Patent Number: 6,051,411
[45] Date of Patent: Apr. 18, 2000

[54] MICROORGANISMS IMMOBILIZED IN CHITOSAN CROSSLINKED WITH LIGNOSULPHONATE FOR PURIFICATION OF WASTE WATER

[75] Inventors: Buris Turtakovsky; Luca Petti; Serge Gulot, all of Montreal, Canada

[73] Assignee: National Research Council of Canada, Ottawa, Canada

[21] Appl. No.: 08/934,571

[22] Filed: Sep. 19, 1997

Related U.S. Application Data

[60] Provisional application No. 60/026,329, Sep. 20, 1996.
[51] Int. Cl.⁷ .......................... C12N 11/10; C12N 11/02; B09B 3/00
[52] U.S. Cl. ........................ 435/178; 435/177; 435/262.5
[58] Field of Search ..................................... 435/134, 177, 435/178, 262.5

[56] References Cited

U.S. PATENT DOCUMENTS

| | | | |
|---|---|---|---|
| 4,760,024 | 7/1988 | Lantero, Jr. | 435/178 |
| 5,284,754 | 2/1994 | Bayer et al. | 435/47 |
| 5,405,764 | 4/1995 | Harder et al. | 435/161 |

*Primary Examiner*—David M. Naff
*Attorney, Agent, or Firm*—J. Wayne Anderson

[57] ABSTRACT

Microorganisms which may be in the form of homogenated anaerobic sludge are immobilized in a polymeric gel matrix containing chitosan and lignosulphonate. A mixture of chitosan solution and a microorganism is added dropwise to a solution of lignosulphonate to crosslink chitosan droplets and form beads of chitosan/lignosulphonate matrix membrane encapsulating the microorganism. Alternatively, the mixture is added to a water-insoluble organic phase to form chitosan beads in an emulsion, and to the emulsion is added a lignosulphonate solution to crosslink the beads and form a chitosan/lignosulphonate matrix membrane encapsulating the microorganism. In another embodiment, anaerobic bacteria in the form of granules are encapsulated in the chitosan/lignosulphonate matrix membrane and the membrane contains another bacterial specie(s). Waste water containing biodegradable polychlorinated aliphatic hydrocarbons is purified by contacting with microorganisms including anaerobic and methanotrophic species encapsulated in beads of the chitosan/lignosulphonate matrix membrane. Reductive dechlorination is effected by the anaerobic species and aerobic mineralization of intermediates is effected by the methanotrophic species which may produce methane monooxygenase.

18 Claims, 3 Drawing Sheets

MICROORGANISMS IMMOBILIZED IN CHITOSAN CROSSLINKED WITH LIGNOSULPHONATE FOR PURIFICATION OF WASTE WATER

This application claims priority from U.S. Ser. No. 60/026,329 filed Sep. 20, 1996.

BACKGROUND OF THE INVENTION

This invention relates to the immobilization of biologically active materials, e.g. bacteria, and in particular to the immobilization of such materials in a polymeric gel matrix comprising chitosan (a high molecular weight polysaccharide) and lignosulphonate.

Biotransformation of chlorinated aliphatics is a multi-step process that can be carried out under both aerobic and anaerobic conditions. The rate of anaerobic degradation of these compounds decreases with the removal of chlorine from the molecules while the degradation rate under aerobic conditions increases (Gerritse et al, 1995)[1]. Thus, the removal of chlorinated aliphatics is a good candidate for the coupling of aerobic and anaerobic biotransformations in an immobilized system.

DESCRIPTION OF THE PRIOR ART

Effective bacterial associations for sequential degradation of complex compounds exist in nature, however, in a reactor slower growing species can be replaced by faster growing ones. This competition problem can be avoided using species immobilization in a polymer matrix. Polyvinyl alcohol (PVA), agarose, k-carrageenan, alginate and chitosan are among the most commonly used polymers for cell immobilization (O'Reilly and Scott, 1995)[2].

Biological wastewater treatment however, is quite different from controlled cultivations with well-defined medium: the influent often contains various ions that may interact with the polymer. Consequently, none of the above mentioned polymers would be considered ideal for this purpose. Moreover, relatively high concentrations of the polymer are required in most cases. For example, with PVA 15–25% w/v is required.

In another prior art reference, U.S. Pat. No. 4,647,536 of Mosbach and Nilsson, a method of immobilizing biomaterials is described, in which the biomaterials in aqueous solution are dispersed in a water-insoluble dispersing medium. The dispersing medium is selected, based upon the biomaterial of interest. Control of the polymer bead size is of particular interest. In one specific example, chitosan is used as the immobilizing polymer for insensitive biomaterials such as certain proteins, which can be linked covalently by cross-linking to the polymer with formaldehyde after they have been immobilized in the polymer.

SUMMARY OF THE INVENTION

In this work we utilize a newly developed procedure of cell immobilization in a polymer matrix of a high molecular weight polysaccharide polymer e.g. chitosan, and lignosulphonate. To illustrate the efficacy of the resulting immobilized material, we use a mixed bacterial system for tetrachloroethylene (PCE) dechlorination. The system combines reductive dechlorination of PCE by methanogenic species with aerobic mineralization of the intermediates by methanotrophic bacteria.

According to a first aspect of the invention, a method is provided for the immobilization of biologically active materials, comprising (a) providing an aqueous solution of chitosan and an acid, (b) adding a biologically active material to the solution, while maintaining the pH in the range of 4.0 to 5.0 to form a mixture, (c) adding the mixture dropwise to an aqueous solution of lignosulphonate, while maintaining the pH in the range of 7.0 to 8.0 by means of a buffer, to form beads of a chitosan/lignosulphonate matrix membrane encapsulating them biologically active material, and (d) stirring to harden the beads.

According to another aspect of the invention, a method is provided for the purification of waste water containing biodegradable polychlorinated aliphatic hydrocarbons, comprising contacting the waste water with microorganisms capable of biodegrading such hydrocarbons, said microorganisms being encapsulated in beads at a chitosan/lignosulphonate matrix, whereby reductive dechlorination is effected by anaerobic species, and aerobic mineralization of intermediates is effected by methanotrophic species.

DESCRIPTION OF THE PREFERRED EMBODIMENTS

Materials and Methods

Chemicals and equipment

Figure 1:
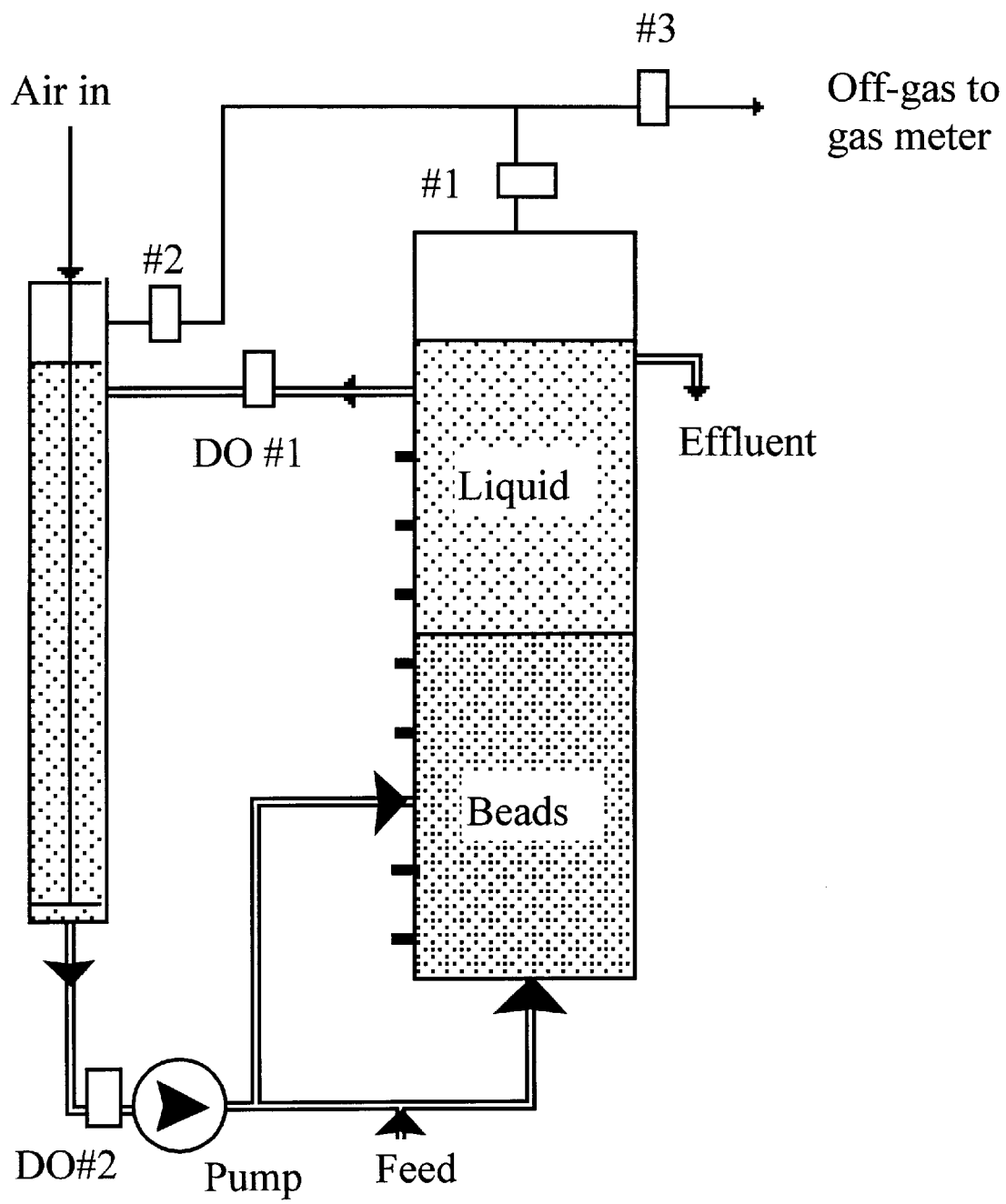
FIG. 1 is a side elevation in perspective of a bioreactor setup used to illustrate an application of the invention.

Chitosan (high molecular weight) was purchased from Fluka Chemical Corp. (Ronkonkoma, N.Y.). Lignosulphonate (lignosite™ 458) and Lignin (Indulin™ AT) were provided at no charge by Georgia-Pacific Corporation (Bellingham, Wash.) and Paprican (Pointe-Claire, Quebec), respectively. All other chemicals were of reagent grade.

PCE in the gas and liquid phases was determined using a Sigma 2000 GC with a FID detector (Perkin-Elmer, Norwalk, Conn.) as described in Kuang et al (1994)[3], the disclosure of which is incorporated herein by reference. The inorganic chloride concentration was determined using the Mercuric Thiocyanate method.

Microorganisms and media

Anaerobic sludge was obtained from an Upflow Anaerobic Sludge Bed (UASB) reactor treating wastewater from a food industry (Champlain Industries, Cornwall, Ontario).

The stock nutrient solution contained (g/L): $KH_2PO_4$, 1.73; $K_2HPO_4$, 2.24; $NH_4HCO_3$, 21.36; $(NH_4)_2SO_4$, 1.64; yeast extract, 2.0; $CH_3COONa.3H_2O$, 340; $CH_3COOH$ (glacial) 153.

Immobilization procedure

According to the first aspect of the invention, homogenized anaerobic sludge is mixed with a solution of chitosan (1–1.5% w/v) in a glacial acetic acid solution while maintaining a pH in the range of 4.0–5.0. The mixture is then added dropwise to an aqueous solution of lignosulphonate (8–12% w/v) preferably about 10% w/v, to form beads of the chitosan/lignosulphonate matrix encapsulating the bacteria, and stirred for 1–3 hours in order to harden the beads. During the dropwise addition of the chitosan/cells mixture the pH of the lignosulphonate solution is maintained at pH 7–8 by the addition of a suitable buffer e.g. tris buffer. After the beads harden for 1–3 hours, they are washed with distilled water.

Effectiveness of this immobilization procedure was dependent upon two major factors: the concentration of lignosulphonate and the pH of the hardening solution. Note, that the mixture of sludge and chitosan preferably had a pH of 4.5 and its injection into the lignosulphonate solution decreased the pH. Consequently, a pH-controller was installed to maintain a constant pH at a pre-set value. Overall, the best results were obtained using 10% w/v lignosulphonate solution and a pH at around 8.

Alternatively, micro-encapsulation within cross linked chitosan/lignosulphonate membranes can be performed by an emulsification technique as follows: Bacteria is added to aqueous chitosan (1–1.5% w/v). The chitosan/cell mixture is dispersed into a non-toxic water-insoluble organic phase e.g., mineral oil, canola oil, soybean oil and the like to form chitosan beads. An emulsion is formed by intensive stirring. Membrane formation is initiated by the addition of an aqueous lignosulphonate solution (8–12% w/v). In effect, aqueous and oil phases are formed. The chitosan beads migrate into the aqueous lignosulphonate phase and harden. Microcapsules are recovered by settling and decantation or by centrifugation and washed with water.

It will be appreciated by those skilled in the art that he procedures described above could also be used for immobilization of microbial species other than those present in anaerobic sludge.

Alternatively, anaerobic granules can be coated with chitosan which contains another bacterial specie(s). This is done by mixing granules, aqueous chitosan (1–1.5% w/v), and a third specie(s) and then dispersing this mixture (i.e. air sparging) in a solution of (8–12% w/v, preferably 10%, lignosulphonate. The end product is anaerobic granules coated with a chitosan/lignosulphonate matrix membrane encapsulating the other bacterial specie(s).

Reactor setup and operation

Chitosan-immobilized sludge was cultivated in an Upflow Sludge Bed and Filter (UBF) reactor with a working volume of 1.2 L connected to an aeration column with a liquid volume of 0.5 L (FIG. 1). The reactor was operated with a hydraulic retention time of 20 h, a liquid upflow velocity of 2–6 m/h and temperature of 25° C. The pH was maintained at a level of 7.3 ±0.1 using a Tris-base solution.

Results and Discussion

Figure 2:
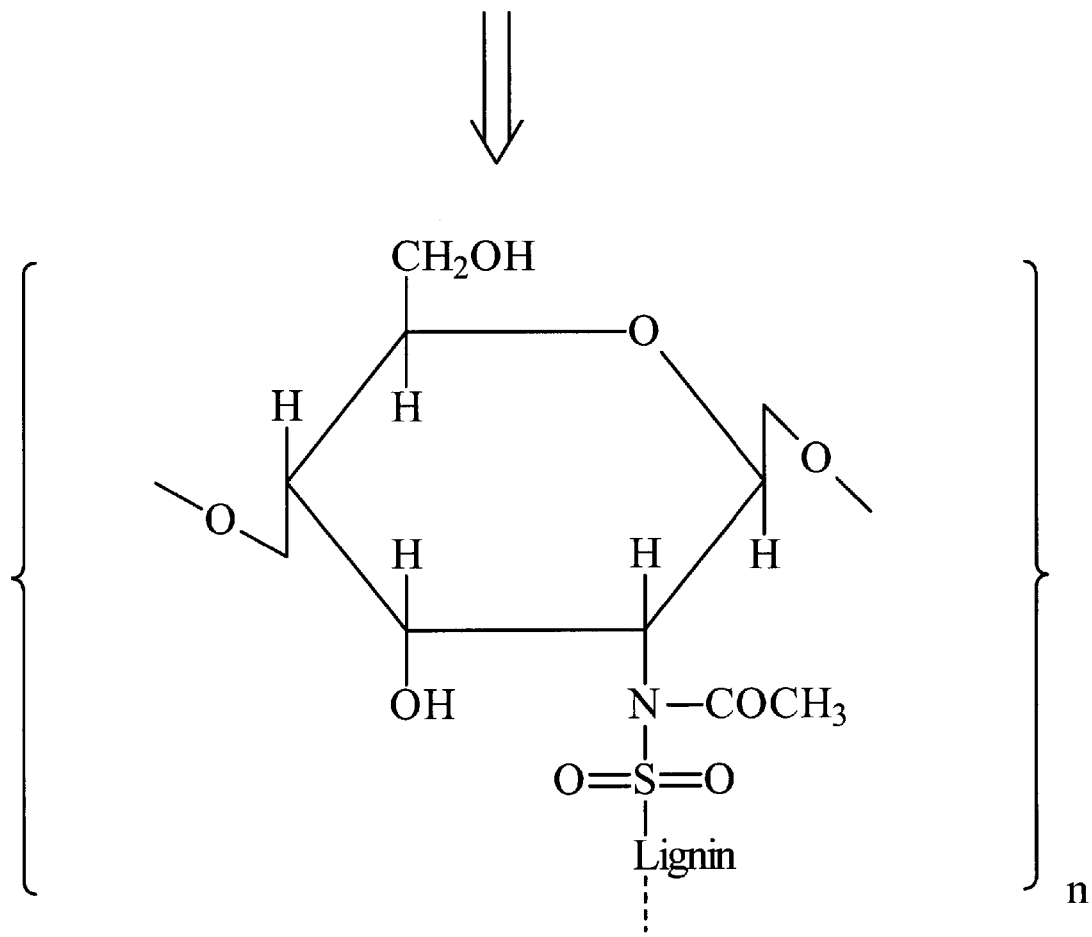
FIG. 2 illustrates a proposed reaction mechanism for the formation of a cross-linked polymer/lignosulphonate matrix according to the invention.

FIG. 2 shows the chemical structure of chitosan polymerized with lignosulphonate. It is hypothesized, that the amino groups of chitosan react with the acidic sulfonic-groups of lignosulphonate to form sulfonylamide linkages. Lignosulphonate is not a defined structure. Other acidic groups in lignin such as phenolics (—OH) and/or carboxylic groups may also react with the basic $NH_2$ groups of chitosan to form amide linkages (—NH—C=O). Since initial attempts of polymerization with lignin failed to give stable beads we believe the alternative cross-linking mechanisms were not important.

Figure 3:
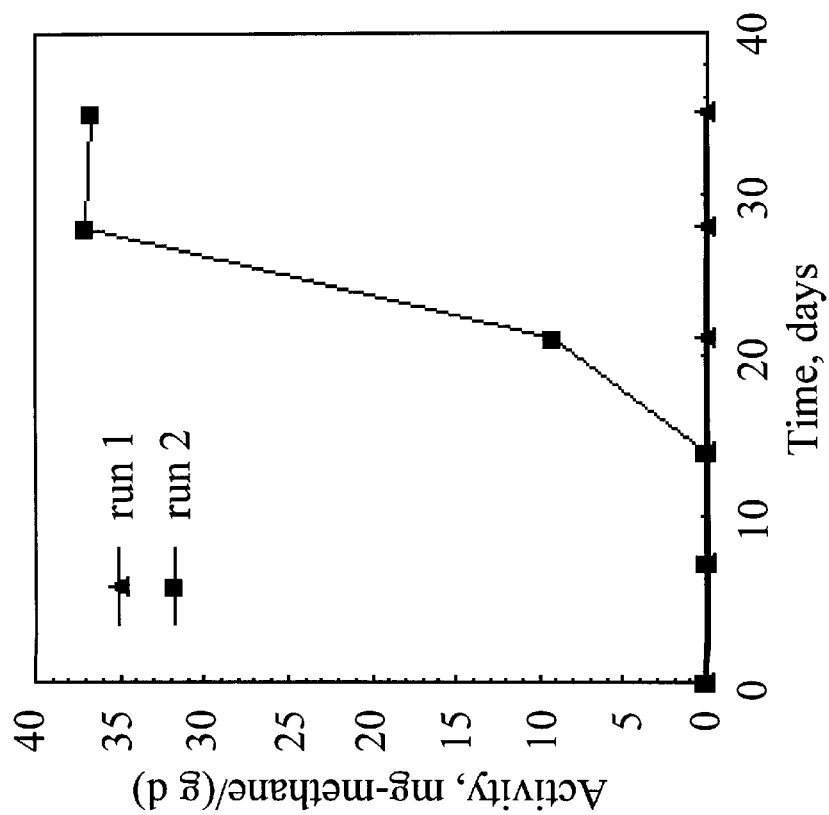

The chitosan-lignosulphonate bioparticles loaded with anaerobic sludge were tested in the modified UBF reactor with aeration column. Two runs were performed. In the first run a low aeration rate (~7 L/day) was applied and PCE was not fed to the reactor. The second run was performed at a higher aeration rate (~10 L/day). The concentration of PCE in the influent during this run was varied from 10 to 30 mg/L. The acetate loading rate in the reactor was maintained at a level of 2.0 g/(L day). It was proposed, that a steep oxygen gradient would protect anaerobic bacteria in the interior pad of the bead while allowing for aerobic metabolism if the shell of the bead. As expected, the methane production rate was inversely related to the aeration rate (data not shown). Moreover due to high bulk oxygen concentration in the second run, methanotrophic bacteria proliferated as indicated by the batch activity test of methane consumption (FIG. 3).

Figure 4:
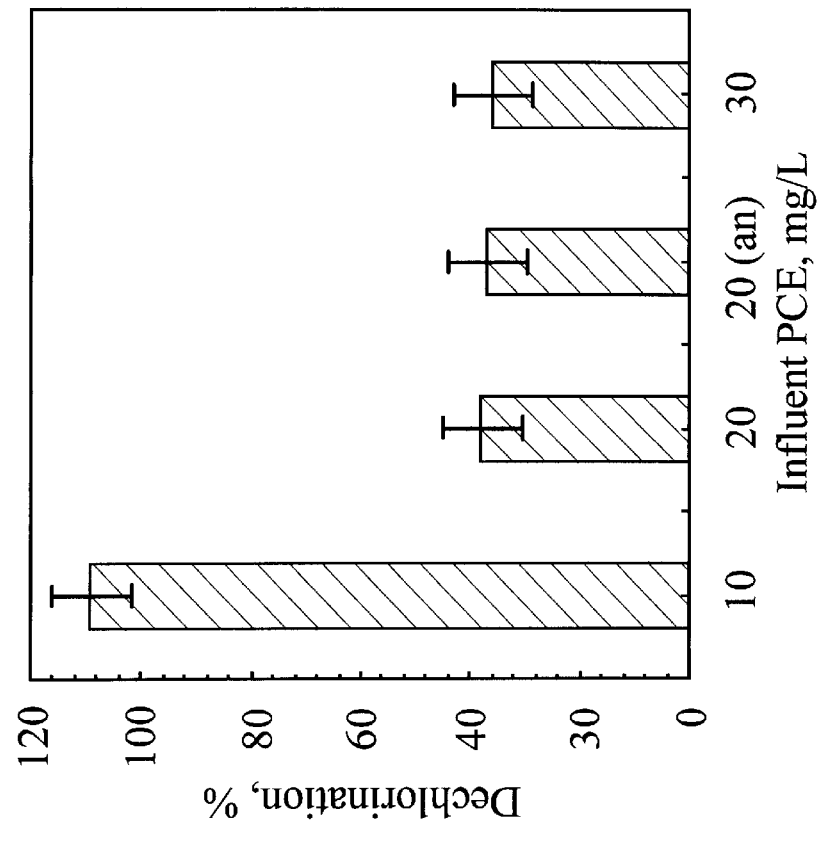
FIGS. 3 and 4 are graphs which illustrate the effectiveness of bacteria immobilized in a polymer/lignosulphonate matrix according to the invention, in the treatment of waste water contaminated with PCEs.

FIG. 4 demonstrates the effectiveness of PCE-dechlorination using the coupled system. At a low PCE-loading rate (10 mg/L of PCE in the influent) near complete dechlorination of PCE was achieved. With increasing influent PCE concentrations the percent dechlorination based on the total PCE fed decreased. When the reactor was converted into an anaerobic unit the percent dechlorination did not change. Concurrently the intermediates dichloroethylene and vinyl chloride were detected in the effluent. This suggests that the initial step of PCE-conversion into trichloroethylene (TCE) by methanogens is not rate limiting while the wild-type methanotrophic bacteria were not capable of fast mineralization of the intermediates. Literature reviews show that only methanotrophs having soluble methane monooxygenase (sMMO) enzyme are capable of effective dechlorination. This enzyme has broad specificity resulting in high rates of dechlorination of TCE and other chlorinated compounds by co-metabolism (McFarland et al, 1992)[4]. In subsequent experiments anaerobic sludge was enriched in methanotrophic species (*Methylosinus sporium*). containing the sMMO plasmid. In these experiments near complete dechlorination of PCE was achieved (data not shown).

Conclusions

A new method of sludge immobilization in chitosan-lignosulphonate matrix was developed. This method has the following advantages: (i) simple and low-cost immobilization procedure; (ii) mild immobilization conditions; (iii) high stability of bioparticles. When compared to the procedure of sludge immobilization in PVA that requires 10–15% w/v concentration of the polymer, the newly developed method uses only 1–1.5% w/v solution of chitosan. No sign of bead disintegration was observed over the five-week period of reactor operation.

Effective association of methanogenic and methanotrophic, bacteria was established. At high oxygenation rates wild-type methanotrophs proliferated in the polymer matrix. These species, however, were not capable of complete dechlorination of chlorinated compounds like TCE, DCE and vinyl chloride.

References

1. Gerritse, J., Renard, V., Visser, J, Gottschal, J. C. (1995) Complete Degradation of Tetrachloroethene by Combining Anaerobic Dechlorinating and Aerobic Methanotrophic Enrichment Cultures. *Appl. Microbiol. Biotechnol*, 43, 920–928
2. O'Reilly, A. M. and Scott, J. A. Defined Coimmobilization of Mixed .Microorganism Cultures (1995) *Enzyme Microb. Technol*, 17, 636–64
3. Guiot, S. R., Kuang, X., Beaulieu. C., Corriveau, A., Hawari, J. A. Anaerobic and aerobic/anaerobic treatment for tetrachloroethylene(PCE). In: Bioremediation Series, Bioremediation of Chlorinated Solvents (Hinchee, R, Leeson, A and Semprini, L., eds.), Battelle Press, Columbus, Ohio, 1995, 3(4): 191–198
4. McFarland, M. J., Vogel, C. M. and Spain, J. C. Methanotrophic Cometabolism of Trichloroethylene (TCE) in a Two Stage Bioreactor System (1995) *Wat. Res.*26, 259–265

We claim:

1. A method for the immobilization of a microorganism, comprising
   (a) providing an aqueous solution of chitosan and an acid, wherein the concentration of chitosan is 1–1.5%/ w/v,
   (b) adding a microorganism, to the solution, while maintaining the pH in a range of 4.0 to 5.0 to form a mixture,
   (c) adding the mixture dropwise to an aqueous solution of lignosulphonate, wherein the concentration of lignosulphonate is 8–12% w/v, while maintaining the pH in the range of 7.0 to 8.0 by means of a buffer, to form beads of a chitosan/lignosulphonate matrix membrane encapsulating the microorganism, and
   (d) stirring to harden the beads.

2. A method according to claim 1, wherein the concentration of lignosulphonate in step (c) is about 10% w/v.

3. A method according to claim 2, wherein the acid is glacial acetic acid, and the pH in step (b) is about 4.5.

4. A method according to claim 3, wherein the buffer is tris buffer.

5. A method according to claim 4, wherein the microorganism comprises bacteria.

6. A method according to claim 5, wherein homogenated anaerobic sludge comprises the bacteria.

7. A method for the immobilization of a microorganism, comprising
   (a) providing an aqueous solution of chitosan, wherein the concentration of chitosan is 1–1.5% w/v,
   (b) adding a microorganism to form a mixture,
   (c) adding the mixture to a non-toxic water-insoluble organic phase to form chitosan beads and stirring to form an emulsion, and
   (d) adding to the emulsion formed in (c), an aqueous lignosulphonate solution, wherein the concentration of lignosulphonate solution is 8–12% w/v, to cross-link the beads and form a chitosan/lignosulphonate matrix membrane encapsulating the microorganism.

8. A method according to claim 7, wherein the organic phase is selected from the group consisting of mineral oil, canola oil and soybean oil.

9. A method according to claim 7, wherein the microorganism comprises bacteria.

10. A method according to claim 9, wherein homogenated anaerobic sludge comprises the bacteria.

11. A method according to claim 7, wherein in step (b) the microorganism comprises anaerobic bacteria in the form of granules and another bacterial specie(s), and wherein step (d) includes air sparging, whereby the anaerobic granules are encapsulated in a chitosan/lignosulphonate matrix membrane and the other bacterial specie(s) is is contained in the membrane.

12. A method for the purification of waste water containing biodegradable polychlorinated aliphatic hydrocarbons, comprising
   contacting the waste water with microorganisms including anaerobic and methanotrophic species capable of biodegrading such hydrocarbons, said microorganisms being encapsulated in beads of a chitosan/lignosulphonate matrix, whereby reductive dechlorination is effected by anaerobic species, and aerobic mineralization of intermediates is effected by methanotrophic species.

13. A method according to claim 12, wherein homogenated anaerobic sludge comprises the microorganisms.

14. A method according to claim 13, wherein the microorganisms are enriched in methanotrophic species which produce methane monooxygenase enzyme.

15. A method according to claim 13, wherein the method is effected in a coupled aerobic/anaerobic bioreactor.

16. A method according to claim 15, wherein the bioreactor is of the upflow type.

17. A method according to claim 13, wherein the method is continuous.

18. A method according to claim 13, wherein the polychlorinated hydrocarbon comprises tetrachloroethylene.

* * * * *

UNITED STATES PATENT AND TRADEMARK OFFICE
CERTIFICATE OF CORRECTION

PATENT NO.    : 6,051,411
DATED         : April 18, 2000
INVENTOR(S)   : Boris Tartakovsky; Luca Petti; Serge Guiot It is certified that error appears in the above-indentified patent and that said Letters Patent is hereby corrected as shown below:

On the title page, item [75]

Please correct the spelling of the first and third inventors names.

Attached is a copy of our letter dated March 23, 2000, advising you of your error regarding the spelling of the inventors names.

The first inventor is Boris Tartakovsky and the third inventor is Serge Guiot.

Signed and Sealed this

Tenth Day of April, 2001

*Attest:*

NICHOLAS P. GODICI

*Attesting Officer*    *Acting Director of the United States Patent and Trademark Office*